(12) United States Patent
Bertagnoli et al.

(10) Patent No.: US 8,613,915 B2
(45) Date of Patent: Dec. 24, 2013

(54) ATTENUATED STRAIN OF MYXOMA VIRUS FOR USE AS AN ONCOLYTIC DRUG

(75) Inventors: Stéphane Bertagnoli, Lavernose-Lacasse (FR); Magalie Gretillat, Villeurbanne (FR); Jacqueline Gelfi, Brignoles (FR); Christelle Camus-Bouclainville, Toulouse (FR)

(73) Assignees: Institute National de la Recherche Agronomique, Paris (FR); ECOLE Nationale Veterinaire Toulouse, Tolouse (FR)

( * ) Notice: Subject to any disclaimer, the term of this patent is extended or adjusted under 35 U.S.C. 154(b) by 44 days.

(21) Appl. No.: 13/377,386

(22) PCT Filed: Jun. 11, 2010

(86) PCT No.: PCT/IB2010/052605
§ 371 (c)(1),
(2), (4) Date: Jan. 19, 2012

(87) PCT Pub. No.: WO2010/143160
PCT Pub. Date: Dec. 16, 2010

(65) Prior Publication Data
US 2012/0141427 A1    Jun. 7, 2012

(30) Foreign Application Priority Data
Jun. 11, 2009 (FR) ...................................... 09 02835

(51) Int. Cl.
*A61K 35/76* (2006.01)
*A61K 48/00* (2006.01)

(52) U.S. Cl.
USPC ....... 424/93.1; 424/93.3; 435/350; 435/320.1

(58) Field of Classification Search
None
See application file for complete search history.

(56) References Cited

FOREIGN PATENT DOCUMENTS

| FR | 2736358 | 1/1997 |
|---|---|---|
| WO | 2007/143548 | 12/2007 |

OTHER PUBLICATIONS

Bertagnoli et al. (A) , J. Virol. 1996, vol. 70, No. 8, pp. 5061-5066.*
Pignolet et al. Virology Journal, 2007, published on line pp. 1-5.*
Labudovic, Sequence Mapping of the Californian MSW Strain of Myxoma Virus, Arch. Virol. 149, 553-570, 2004.
International Search Report for PCT/IB2010/052605.

* cited by examiner

*Primary Examiner* — Bao Li
(74) *Attorney, Agent, or Firm* — Morgan, Lewis & Bockius LLP

(57) ABSTRACT

The invention relates to the use of an attenuated vaccinal strain of Myxoma virus, in particular the SG33 strain, as an oncolytic agent.

5 Claims, 3 Drawing Sheets

ATTENUATED STRAIN OF MYXOMA VIRUS FOR USE AS AN ONCOLYTIC DRUG

RELATED APPLICATIONS

Figure 1:
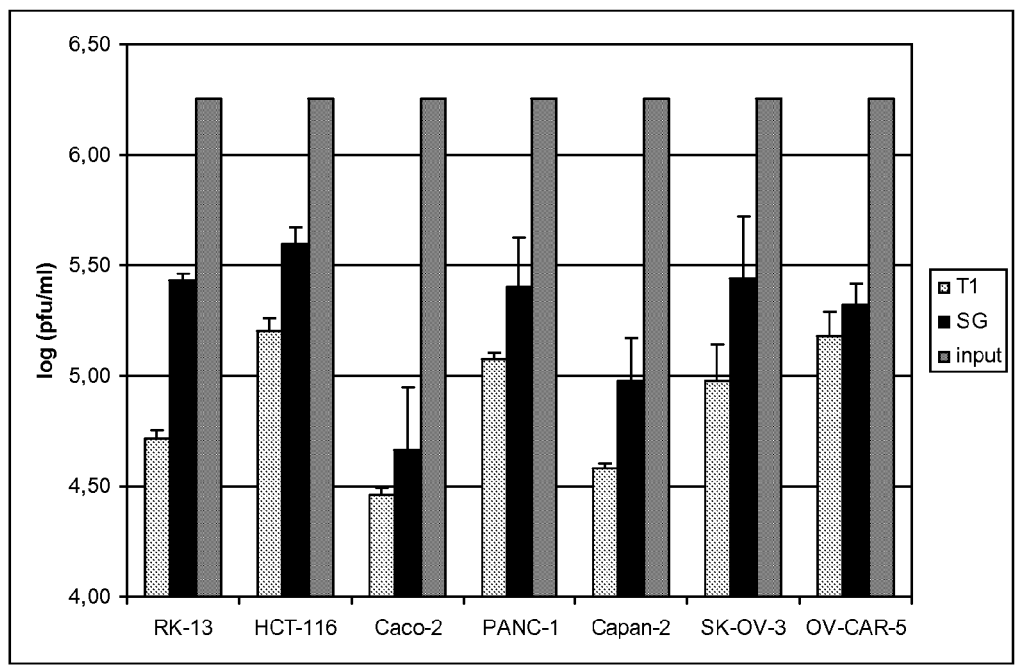

The present application is a U.S. National Phase Application of International Application No. PCT/IB2010/052605 (filed Jun. 11, 2010) which claims priority to French Application No. 0902835 (filed Jun. 11, 2009) which are hereby incorporated by reference in their entirety.

The present invention relates to the use of an attenuated vaccine strain of Myxoma virus as oncolytic agent.

An oncolytic virus is a virus which preferably lyses cancer cells, while having little effect on non-cancer cells. Oncolytic virotherapy constitutes an advantageous therapeutic approach for completing the arsenal of available anticancer therapies.

The myxomatosis virus (MYXV), also called Myxoma virus, belongs to the genus Leporipoxvirus in the Poxviridae family. It is the agent responsible for myxomatosis, a major infectious disease in European rabbits and an endemic disease in Europe. This virus exhibits a narrow host range and is not pathogenic for humans.

The complete sequence of the genome of the Lausanne strain of MYXV (reference pathogenic strain) is known (CAMERON et al., Virology, 264, 298-318, 1999; GenBank NC_001132). This genome consists of a double-stranded linear DNA molecule of about 162 kbp. It contains a highly conserved central region in the Poxviridae family, containing the genes that are essential for viral replication, flanked by more variable regions containing so-called virulence genes, and two inverted terminal repeats (ITR) of 11.5 kpb. It comprises 170 open reading frames in total of which 12 are present in duplicate in the ITRs. Some of the proteins encoded by these 12 reading frames have been identified as constituting virulence factors, interfering with the immune defenses of the host. Mention may be made in particular of serpin Serp1, described as having inhibitory properties on the inflammatory response and complement activation; the viroceptors M-T1, M-T2 and M-T7, described as interfering with chemokines involved in the antiviral response: CC-chemokines in the case of M-T1, TNF in the case of M-T2, and IFN-gamma in that of M-T7; the proteins M-T2, MT4, and MT5, which are thought to constitute inhibitors of apoptosis of the infected cells.

Despite its high host-specificity, it has been shown that MYXV could productively infect a wide variety of tumoral cells in vitro (SYPULA et al., Gen Ther Mol Biol, 8, 103-114, 2004), and that it had an oncolytic activity in human pancreatic adenocarcinoma cells in vitro (WOO et al., Ann Surg Oncol, 15, 2329-35, 2008), and in murine models of gliomas, of medulloblastomas and of human rhabdoid tumors in vivo (LUN et al., Cancer Res, 65, 9982-90, 2005; LUN et al., Cancer Res, 67, 8818-27, 2007; WU et al., Clin Cancer Res, 14, 1218-27, 2008). It has thus been proposed to use it as oncolytic agent (PCT application WO2004/078206). The PCT application WO2007/143548, and BARRETT et al. (J. Neurovirol, 13, 549-560, 2007), describe trials of inactivation of certain Myxoma virus genes encoding proteins involved in cell tropism in relation to rabbit cells (M11L, M063, M135, M136, M-T2, M-T4, M-T5 and M-T7), with the aim of testing the effects of this inactivation on the capacity of Myxoma virus to infect and kill human glioma cells, and to use these Myxoma viruses for the treatment of cancer, in particular of glioma; the Myxoma viruses, in which the M063 gene or the M135 gene has been inactivated, replicate in the glioma cells more efficiently than the wild-type virus, and reduce the viability of the glioma cells which they have infected.

It has been reported that the permissiveness of human tumor cells to infection by a Myxoma virus was linked, on the one hand, to the level of activation of the serine/threonine kinase Akt-1/PKB in the tumor cell and, on the other hand, to the expression in the virus of a functional M-T5 protein, which is capable of inducing the phosphorylation and activation of Akt-1/PKB. It is thus possible to distinguish 3 types of tumor cells: in the type I cells, Akt-1/PKB is constitutively strongly activated, and these cells are permissive to infection by a Myxoma virus even if the latter does not express M-T5; in the type II cells, the basal level of Akt-1/PKB activation is weak, but it is activated by the interaction with M-T5: these cells are permissive only to the Myxoma viruses expressing M-T5; finally, in the type III cells, the basal level of Akt-1/PKB activation is also weak, and it is not activated by M-T5: these cells are not permissive to the Myxoma viruses. The treatment of non-permissive tumor cells with an agent capable of increasing the activation of Akt-1/PKB, such as rapamycin, makes it possible to greatly improve their sensitivity to infection by the Myxoma viruses (STANFORD & MCFADDEN, Expert Opin Biol Ther, 7, 1415-25, 2007; LUN et al., Cancer Res, 67, 8818-27, 2007).

The inventors have now observed that an attenuated vaccine strain of Myxoma virus, the SG33 strain, replicates more efficiently and diffuses better in tumor cells, and has a higher oncolytic activity and a broader activity spectrum than a wild-type strain such as the Lausanne strain.

The SG33 strain (CNCM I-1594) is described in patent FR 2736358. The inventors compared the genome of SG33 with that of the reference Lausanne strain, in order to determine what were the differences between these two strains that can affect the production or the function of viral proteins.

They observed that the SG33 strain contains a deletion of about 15 kb in the right-hand portion of its genome. The genes affected by this deletion are listed in table I below:

TABLE I

| Gene name | Position on the genome[a] | Product (GenBank accession number)[a] | Putative function/known homologs |
|---|---|---|---|
| M151R | 146684-147685 | Serp2 (NP_051864) | serpin/SPI 2 of the vaccinia virus |
| M152R | 147688-148488 | Serp3 (NP_051865) | serpin |
| M153R | 148526-149146 | M153R/MV-Lap (NP_051866) | scrapin |
| M154L | 149883-149239 | gp120-like (NP_051868) | unknown function/M2 of the vaccinia virus |
| M156R | 149997-150305 | M156R (NP_051869) | resistance to IFNs/K3L of the vaccinia virus; eIF2 alpha |
| M008.1R | 150313-151422 | Serp1 (NP_051870) | serpin |
| M008R | 151400-152947 | M-T8 (NP_051871) | protein with the motif Kelch/A55R of the vaccinia virus |
| M007R | 152998-153789 | M-T7 (NP_051872) | receptor for IFN-gamma/B8R of the vaccinia virus |

TABLE I-continued

| Gene name | Position on the genome[a] | Product (GenBank accession number)[a] | Putative function/known homologs |
|---|---|---|---|
| M006R | 153826-155355 | M-T6 (NP_051873) | protein with the motif Kelch/A55R of the vaccinia virus |
| M005R | 155391-156842 | M-T5 (NP_051874) | protein with the motif ankyrine/B4R of the vaccinia virus |
| M004.1R | 156862-157134 | M4.1 (NP_051875) | unknown function/C2L of the swinepox virus |
| M004R | 157138-157851 | M-T4 (NP_051876) | virulence factor/B9R of the vaccinia virus |
| M003.2R | 158084-158425 | M3.2 (NP_051877) | unknown function/T3C of the capripoxvirus |
| M003.1R | 158495-158950 | m3.1L/R (NP_051878) | unknown function/B15R of the vaccinia virus |
| M002R | 159129-160109 | M-T2 (NP_051879) | soluble receptor for TNF alpha/B28R of the vaccinia virus |
| M001R | 160189-160971 | M-T1 (NP_051880) | protein for binding the chemokines/B29R of the vaccinia virus |

[a]The positions on the genome and the GenBank accession numbers are those of the corresponding proteins and genes in the reference Lausanne strain.

The genes M151R and M001R are only partially deleted, giving rise to inactive truncated proteins. The genes M152R, M153R, M154L, M156R, as well as the genes for the right-hand ITR M008.1R, M008R, M007R, M006R, M005R, M004.1R, M004R, M003.2R, M003.1R, and M002R are completely deleted. The proteins encoded by the genes M152R, M153R, M154L, M156R, are therefore absent; by contrast, another copy of the genes M008.1R, M008R, M007R, M006R, M005R, M004.1R, M004R, M003.2R, M003.1R, and M002R being present in the left-hand ITR, it is possible to assume that the corresponding proteins are still produced, although probably in a smaller quantity.

Another difference between the genome of the SG33 strain and that of the Lausanne strain is at the level of the M011L gene (positions 14125-13628 in the genome of the Lausanne strain), encoding an inhibitor of apoptosis (M11L, GenBank NP_051725).

In the SG33 strain, this gene is interrupted by a stop codon, leading to the appearance of two new potential reading frames and to the production of two truncated proteins, M11aL (corresponding to the first 32 amino acids of M11L) and M11bL (starting with methionine at position 52 of M11L). The M11aL protein is probably inactive, and it is possible that some of the M11L functions are altered in M11bL.

The subject of the present invention is an attenuated Myxoma virus in which the genes M151R, M152R, M153R, M154L, M156R, and M001R are inactive, for use as an oncolytic medicament.

According to a particular embodiment of an attenuated Myxoma virus which can be used in accordance with the invention, one or more of the genes M008.1R, M008R, M007R, M006R, M005R, M004.1R, M004R, M003.2R, M003.1R, and M002R of said Myxoma virus may additionally be inactive. Optionally, said attenuated Myxoma virus additionally carries in the M011L gene a mutation resulting in the expression of a mutant M11L protein, free of the 51 N-terminal amino acids of the native M11L protein.

Preferably, said Myxoma virus is the SG33 virus (CNCM 1-1594).

An attenuated Myxoma virus which can be used in accordance with the invention may be obtained from a virulent wild-type Myxoma virus, especially by deletion of the genes M151R, M152R, M153R, M154L, M156R, and M001R, and preferably by the additional deletion of the genes M008.1R, M008R, M007R, M006R, M005R, M004.1R, M004R, M003.2R, M003.1R, and M002R. For each of the relevant genes, the deletion should be of adequate size for the protein produced by this gene to be completely inactive, and will preferably include the entire gene. Optionally, it is additionally possible to introduce a mutation into the M011L gene, for example a deletion or a stop codon, resulting in the expression of a mutant M11L protein, free of the 51 N-terminal amino acids of the native M11L protein.

Advantageously, in order to carry out the present invention, it is possible to use a modified attenuated Myxoma virus expressing a gene of interest (for example a therapeutic gene of the herpesvirus Thymidine kinase type, or FCU1, produced from the fusion between the genes encoding Cytosine deaminase and Uracil phosphoribosyltransferase) (ERBS et al, *Cancer Gene Therapy*, 15, 18-28, 2008). Attenuated Myxoma viruses modified so as to express a gene of interest are for example described in patent FR 2736358.

The attenuated Myxoma viruses in accordance with the invention may be used in the treatment of any type of cancer whose cells allow their replication, which can be easily determined using the methods described in the examples below. Their use is particularly advantageous in the context of the treatment of colorectal, pancreatic and ovarian cancers. They may also be used in the context of the treatment of glial tumors, for example glioblastomas.

The attenuated Myxoma viruses used in accordance with the present invention may be administered locally, by intra-tumoral injection. They may also be administered by the general route, in particular by the intravenous route; indeed the fact that they exhibit better diffusion in tumor cell cultures in vitro and greater oncolytic efficiency at a low multiplicity of infection than the wild-type Myxoma virus may make it possible to limit the consequences of loss of viral particles before reaching the target tumor region.

The present invention will be understood more clearly with the aid of the additional description which follows, which refers to non-limiting examples illustrating the properties of the Myxoma virus SG33, compared with those of a wild-type strain of Myxoma virus.

EXAMPLE 1

Comparison of the Efficiency of Replication of the SB33 Strain and the Wild-type Strain Toulouse 1 in Human Tumor Cells The SG33 strain is a Myxoma virus strain attenuated by serial passages on a cell culture; the TOULOUSE 1 strain is a conventional virulent strain of Myxoma virus, equivalent to the reference LAUSANNE strain. The SG33 and TOULOUSE 1 strains are described in patent FR 2736358, and have been deposited at the Collection Nationale de Cultures de Micro-organismes (C.N.C.M.) under the numbers I-1594 and I-1592, respectively.

The human tumor cell lines used are listed in table II below.

TABLE II

| Cell line | Reference collection (name) | Cell type | Basal level of activation of Akt | Reference (activation of Akt) |
|---|---|---|---|---|
| RK-13 | ATCC (CCL-37) | rabbit kidney cells | — | — |
| HUV-EC-C | ATCC (CRL-1730) | normal human endothelial cells | — | — |
| HCT-116 | ATCC (CCL-247) | human colorectal adenocarcinoma | high | 1, 2 |
| Caco-2 | ATCC (HTB-37) | human colorectal adenocarcinoma | high | 2 |
| PANC-1 | ATCC (CRL-1469) | human pancreatic adenocarcinoma | high | 3, 4 |
| Capan-2 | ATCC (HTB-80) | human pancreatic adenocarcinoma | high | 3, 4 |
| SK-OV-3 | ATCC (HTB-77) | human ovarian adenocarcinoma | high | 5 |
| OV-CAR-5 | NCI60 (OV-CAR-5) | human ovarian adenocarcinoma | low | 5 |

ATCC: American type Culture Collection
NCI60: Collection of 60 tumoral cell lines of the National Cancer Institute of the United States
(1) WANG et al., PNAS, 103, 4640-5, 2006;
(2) SHIMIZU et al, Clin Cancer Res. 11, 2735-46, 2005;
(3) BONDAR et al, Mol Cancer Therap, 12, 989-97, 2002;
(4) WOO et al, Ann Surg Oncol, 15, 2329-35, 2008;
(5) ALTOMARE et al, Oncogene, 23, 5853-7, 2004.

Each cell line ($1.2 \times 10^6$ cells) was infected with the Toulouse 1 or SG33 strains at an M.O.I. (multiplicity of infection) of 3 (adsorption 90 minutes at 4° C., then incubation at 37° C., in an atmosphere containing 5% $CO_2$) and then the viral production was measured 4, 12, 24 and 48 hours post-infection. For that, at each kinetics point, the cells were frozen, and were then subjected to three freeze-thaw cycles, and the supernatant applied to RK13 cells for titration by the plaque method. The replication efficiency is determined by the ratio between the initial viral titer, immediately after the adsorption at 4° C. (T0) and the viral titer 48 hours post-infection (T48).

The results (T48/T0 ratio) obtained from the titration curves (performed in triplicate) are presented in table III below.

TABLE III

| Cell line | Infection Toulouse 1 | Infection SG33 |
|---|---|---|
| RK-13 | 54.81 | 92.59 |
| HUV-EC-C | 0.22 | 2 |
| HCT-116 | 1.15 | 17.13 |
| Caco-2 | 2.71 | 30.36 |
| PANC-1 | 3.67 | 4.33 |
| Capan-2 | 3.96 | 5.28 |
| SK-OV-3 | 3.34 | 5.71 |
| OV-CAR-5 | 4.71 | 23.36 |

The results obtained from the titration curves (performed in triplicate) show that the SG33 strain has a higher multiplicative capacity, which manifests itself by a significantly better yield.

Adsorption experiments were additionally carried out on the cell lines RK-13, HCT-116, Caco-2, PANC-1, Capan-2, SK-OV-3, and OV-CAR-5. $10^6$ cells were infected at an M.O.I. of 5 with either of the viruses (Toulouse 1 or SG33) at 4° C., and then washed twice before being frozen and being subjected to three freeze-thaw cycles. The adsorbed viruses are then titrated on RK13 cells.

The results representing the mean of three independent experiments are illustrated by FIG. 1. On the x-axis: strains tested; on the y-axis: viral titer; T1=Toulouse 1; SG=SG33; input=theoretical quantity of virus in each inoculum.

These results show that the SG33 strain is adsorbed more efficiently than the Toulouse 1 strain on all the cell lines tested.

EXAMPLE 2

Comparison of the Kinetics of Diffusion of the Toulouse 1 and SG33 Viruses Expressing Beta-Galactosidase In order to monitor viral diffusion within the infected cellular lawns, Toulouse 1 and SG33 viruses expressing Beta-galactosidase, after insertion of the Lac Z gene, under the control of a poxviral promoter, into the TK locus of the viral genomes (BERTAGNOLI et al., 1996, J. Virol., 70(8):5061-6) were used.

Each cell line (tumor lines HCT-116, PANC-1, and SK-OV-3, and the control lines HUV-EC-C and RK13), at 90-95% confluence, was infected at an M.O.I. of 0.00005 and the number of viral foci (stained blue) per well ($10^6$ cells) was counted at 24, 48, 72 and 96 hours post-infection (performed in triplicate), after fixing the corresponding wells and application of a layer of agar containing X-Gal.

Figure 2:
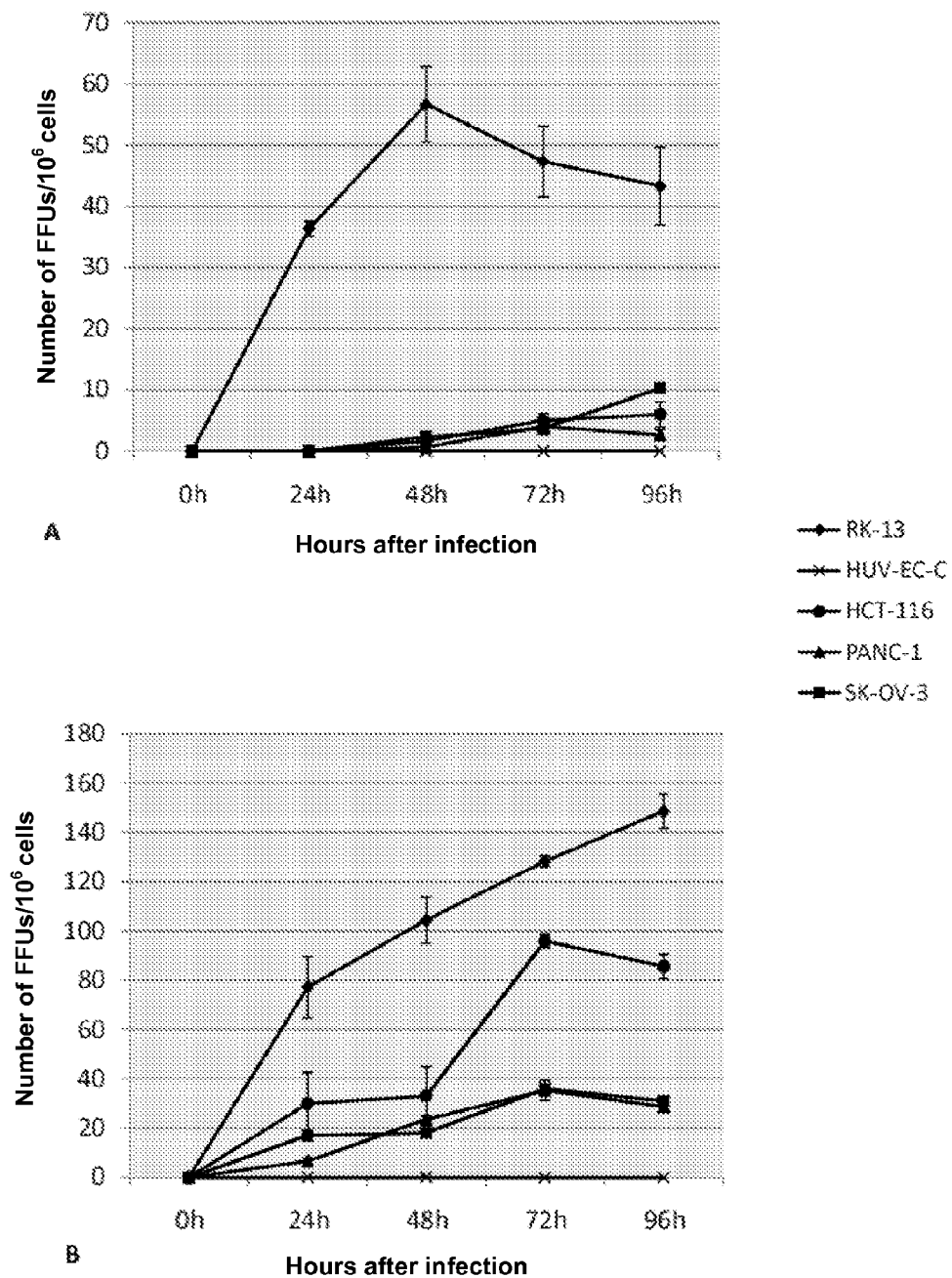

The results are illustrated by FIG. 2. (Toulouse 1: graph A; SG33: graph B). On the x-axis: time after infection; on the y-axis: Foci Forming Unit (FFU) for $10^6$ cells.

These results show that the SG33 strain diffuses more efficiently from 24 post-infection than the Toulouse 1 strain for all the cells tested ($p<0.05$, Student test).

EXAMPLE 3

Comparison of the Oncolytic Properties of the Toulouse 1 and SG33 Viruses

The cellular viability was measured by a test with neutral red, 5 days post-infection. For that, the confluent cells cultured in a 96-well plate were infected at an M.O.I of 5, and left to incubate for 5 days. Next, the quantity of viable cells was measured by the absorption of the neutral red (contacting of the cellular lawn for 4 hours with a medium supplemented with 3% neutral red; and then washing of the cells and incubation in the presence of absolute alcohol, the release of the neutral red being monitored by measurement of the OD at 450 nm). The results are expressed in the form of a ratio between the mean of the OD values measured in the wells of infected cells and the mean of the OD values measured in the wells of non-infected cells.

Figure 3:
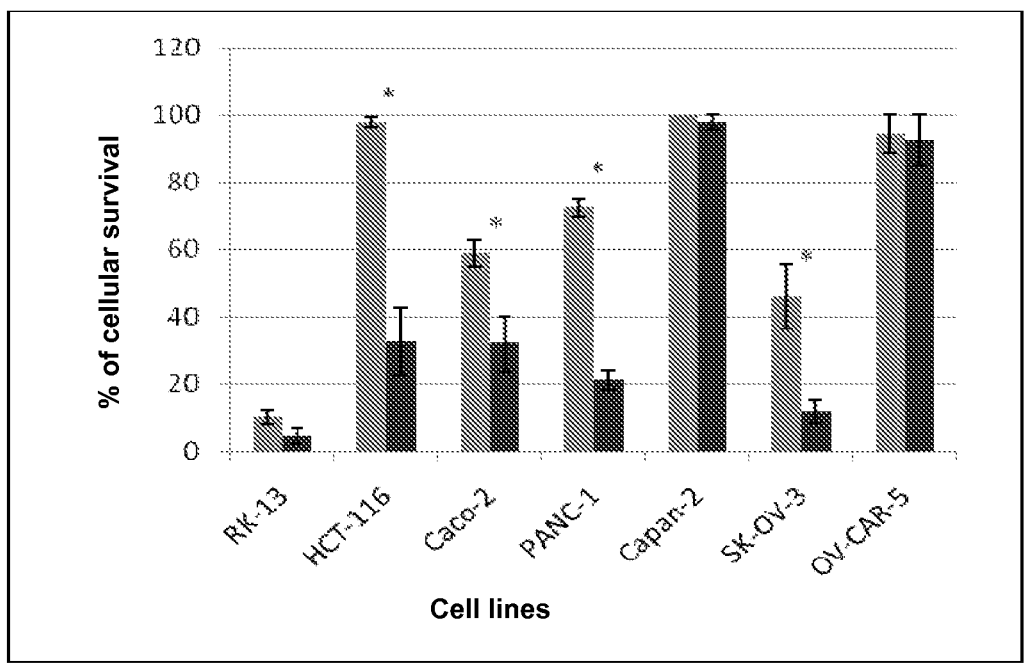

The results (experiments carried out in triplicate) are illustrated by FIG. 3. Infection Toulouse 1: shaded bars; infection SG33: dark bars.

These results show that the percentage of cell survival is significantly different after infection with SG33 compared with the infection with Toulouse 1, for the HCT-116, Caco-2, Panc-1 and SK-OV-3 cells ($p<0.05$, Student test).

The invention claimed is:
1. A method of killing a cancer cell comprising contacting the cell with an attenuated SG33 strain of Myxoma virus deposited with the Collection Nationale de Cultures de Microorganismes (CNCM) under Accession No. 1-1594.

2. The method of claim 1 wherein the cancer cell is present in a human subject.

3. The method of claim 2 wherein the cancer cell is selected from the group consisting of colorectal, pancreatic and ovarian cancer cells.

4. The method of claim 1 wherein the cancer cell is present in a glial tumor.

5. The method of claim 4 wherein the glial tumor is a glioblastoma.

* * * * *